United States Patent
Benton et al.

(10) Patent No.: US 7,207,961 B1
(45) Date of Patent: Apr. 24, 2007

(54) MEDICAL APPARATUS FOR FEET

(76) Inventors: David Benton, 8620 Lindbergh Blvd., Philadelphia, PA (US) 19153; Tamika Benton, 8620 Lindbergh Blvd., Philadelphia, PA (US) 19153

( * ) Notice: Subject to any disclaimer, the term of this patent is extended or adjusted under 35 U.S.C. 154(b) by 61 days.

(21) Appl. No.: 11/268,743

(22) Filed: Nov. 7, 2005

(51) Int. Cl.
*A61F 5/00* (2006.01)

(52) U.S. Cl. .............................. 602/5; 602/23; 602/27; 602/30

(58) Field of Classification Search .................... 2/239, 2/242; 36/9 R, 10, 11, 12, 14; 128/882; 602/26, 30, 5, 27
See application file for complete search history.

(56) References Cited

U.S. PATENT DOCUMENTS

| | | | | |
|---|---|---|---|---|
| 3,863,272 A | | 2/1975 | Guille | |
| 4,651,354 A | * | 3/1987 | Petrey | 2/239 |
| 4,962,762 A | * | 10/1990 | Beekil | 36/154 |
| 5,403,265 A | * | 4/1995 | Berguer et al. | 601/151 |
| 5,617,585 A | * | 4/1997 | Fons et al. | 2/239 |
| 6,606,750 B2 | * | 8/2003 | Solwey | 2/239 |

FOREIGN PATENT DOCUMENTS

JP 61186501 A * 8/1986

* cited by examiner

*Primary Examiner*—Michael A. Brown

(57) ABSTRACT

A medical apparatus is provided. The medical apparatus is designed to be a foot covering that is specially designed for diabetic individuals who may have or be susceptible to medical conditions of the feet. The medical apparatus allows an individual to go outdoors without wearing shoes, because the medical apparatus itself serves as a crude shoe covering over a pair of feet. In addition, the medical apparatus itself can serve as a sock covering, which can then be used when a shoe is placed over an individual's feet.

5 Claims, 2 Drawing Sheets

MEDICAL APPARATUS FOR FEET

BACKGROUND OF THE INVENTION

1. Field of the Invention

This invention relates generally to medical apparatus for feet and, more particularly, the invention relates to a medical apparatus designed to be a foot covering that is specially designed for diabetic individuals who may have or be susceptible to medical conditions of the feet.

2. Description of the Prior Art

U.S. Pat. No. 6,606,750, issued to Solwey, discloses a sock with a fluid absorbing bottom portion for use, especially with diabetics.

U.S. Pat. No. 5,617,585, issued to Fons, discloses a sock with latex rubber embedded fabric to form a protective sole impervious to sharp objects or temperature extremes.

U.S. Pat. No. 3,863,272, issued to Guille, discloses an article of footwear such as a sock with an integral bottom adhered flexible hard plastic sole.

SUMMARY

The present invention concerns that of a new and improved medical apparatus. The medical apparatus is designed to be a foot covering that is specially designed for diabetic individuals who may have or be susceptible to medical conditions of the feet. The medical apparatus allows an individual to go outdoors without wearing shoes, because the medical apparatus itself serves as a crude shoe covering over a pair of feet. In addition, the medical apparatus itself can serve as a sock covering, which can then be used when a shoe is placed over an individual's feet.

There has thus been outlined, rather broadly, the more important features of a medical apparatus that the detailed description thereof that follows may be better understood and in order that the present contribution to the art may be better appreciated. There are, of course, additional features of the medical apparatus that will be described hereinafter and which will form the subject matter of the claims appended hereto.

In this respect, before explaining at least one embodiment of the medical apparatus in detail, it is to be understood that the medical apparatus is not limited in its application to the details of construction and to the arrangements of the components set forth in the following description or illustrated in the drawings. The medical apparatus is capable of other embodiments and being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present medical apparatus. It is important, therefore, that the claims be regarded as including such equivalent constructions insofar as they do not depart from the spirit and scope of the present invention.

It is therefore an object of the present invention to provide a medical apparatus which has all of the advantages of the prior art and none of the disadvantages.

It is another object of the present invention to provide a medical apparatus which may be easily and efficiently manufactured and marketed.

It is another object of the present invention to provide a medical apparatus which is of durable and reliable construction.

It is yet another object of the present invention to provide a medical apparatus which is economically affordable and available for relevant market segment of the purchasing public.

Other objects, features and advantages of the present invention will become more readily apparent from the following detailed description of the preferred embodiment when considered with the attached drawings and appended claims.

DETAILED DESCRIPTION OF THE PREFERRED EMBODIMENTS

Figure 1:
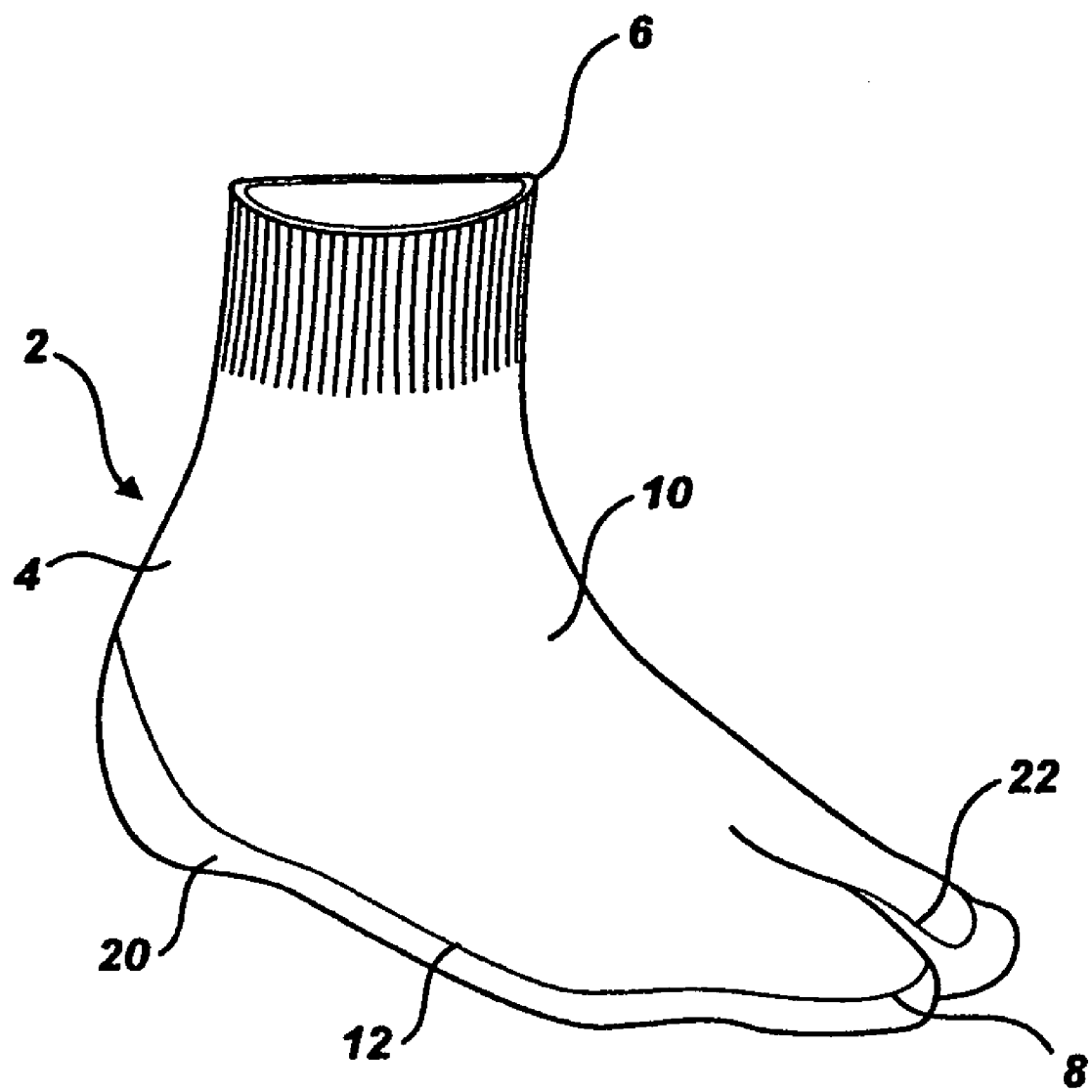
FIG. 1 shows a perspective view of the medical apparatus.
Figure 2:
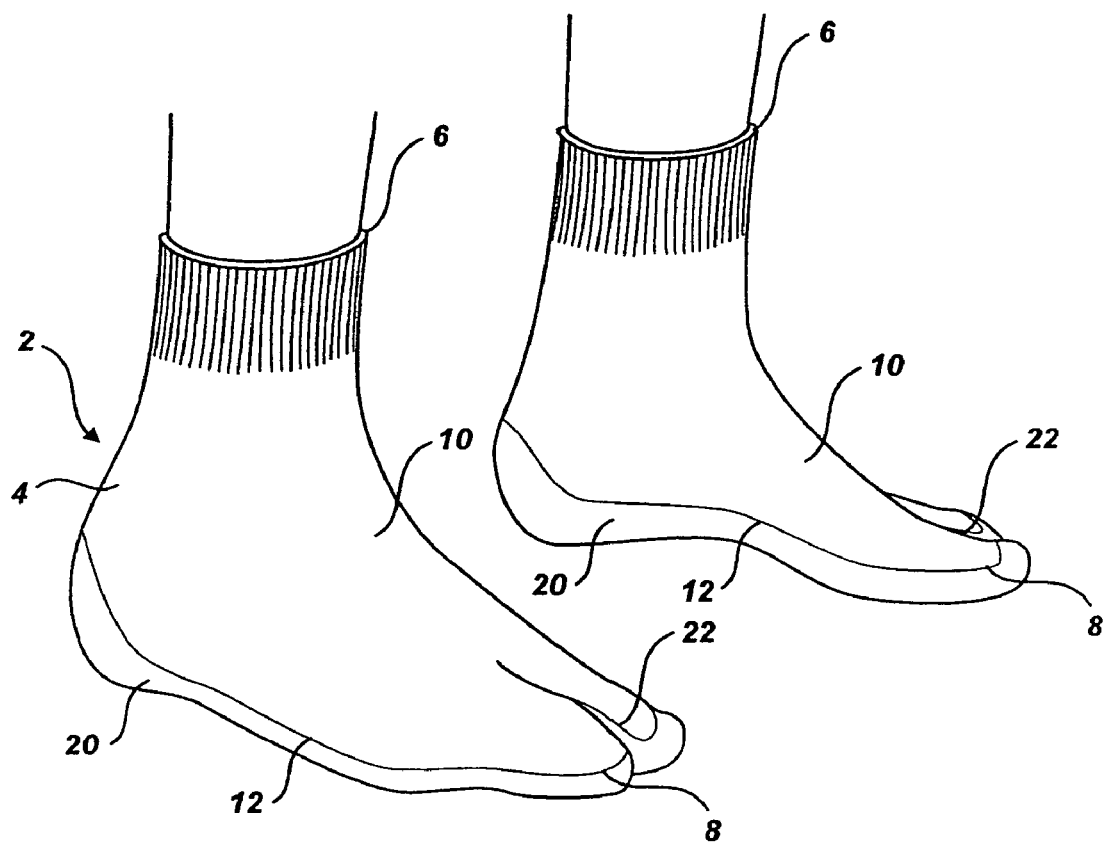
FIG. 2 shows a perspective view of the medical apparatus as it would appear in use.

FIG. 1 shows a perspective view of the medical apparatus 2, while FIG. 2 shows a perspective view of the medical apparatus 2 as it would appear in use. Medical apparatus 2 is essentially a modified sock 4 that has two ends, an open end 6 and a closed end 8.

The sock 4 has two surfaces, a top surface 10 and a bottom surface 12. The bottom surface 12 of each sock 4 of the medical apparatus 2 has a layer of hard plastic 20 essentially coupled with the sock 4. The layer of hard plastic 20 essentially covers the entire bottom surface 12 of each sock 4, and in addition, wraps around about one-half inch toward the top surface of the sock 4.

The closed end 8 of the sock 4 has a cut 22 that travels into the sock 4. The cut 22 is generally to be placed in between an individual's big toe and the $2^{nd}$ toe on their foot. This cut 22 will make it more comfortable for an individual to wear the sock 4 on both feet.

Sock 4 itself can be fabricated from a wide variety of materials. However, the sock 4 preferably is fabricated from a thin, flexible fabric. The preferred fabric to be used in creating the sock 4 is cotton.

In FIG. 2, the medical apparatus 2 can be seen in use on a pair of feet. The medical apparatus 2 would greatly assist people with medical conditions in their feet, especially diabetics. Presently, diabetics must wear shoes when they are outdoors, lest they get their feet infected from cuts, scrapes, bruises, various parasite infections, and even sun burn, which is the leading cause for amputation. With the medical apparatus 2, an individual can still travel outdoors in a limited fashion, yet at the same time, have foot protection that will eliminate or severely reduce the danger to an individual's foot.

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the present invention is to be limited only to the claims except as precluded by the prior art. Moreover, the invention as disclosed herein, may be suitably practiced in the absence of the specific elements which are disclosed herein.

What is claimed is:

1. A medical apparatus for covering the foot, heel, and toes of an individual, the medical apparatus comprising:
   an ankle length sock having an open end, a closed end, a top surface, and a bottom surface; and
   a layer of hard material attached to the bottom surface of the sock, the layer of hard material wrapping around the sock about one-half inch toward the top surface of the sock, the hard material extending upward covering the entire heel, the top surface of the sock over the toes being free from the hard material,
   wherein the sock can be used as a limited shoe in an outdoor setting.

2. A medical apparatus according to claim 1 wherein the layer of hard material attached to the bottom surface of the sock is constructed from plastic.

3. A medical apparatus according to claim 1 wherein each sock is fabricated from a thin, flexible fabric.

4. A medical apparatus according to claim 1 wherein each sock is fabricated from cotton.

5. A medical apparatus according to claim 1 wherein each sock further comprises a cut that travels into the sock, the cut being placed in an area within the sock so that it is located between an individual's big toe and the $2^{nd}$ toe on their foot once the sock is placed on an individual's foot.

* * * * *